United States Patent [19]

Davison et al.

[11] Patent Number: 4,499,025
[45] Date of Patent: Feb. 12, 1985

[54] ELECTROCHEMICAL MAINTENANCE OF CATALYST ACTIVITY

[75] Inventors: John B. Davison; Raymond J. Jasinski, both of Mission Viejo; Pamela J. Peerce-Landers, Huntington Beach, all of Calif.

[73] Assignee: Occidental Chemical Corporation, Niagara Falls, N.Y.

[21] Appl. No.: 371,378

[22] Filed: Apr. 23, 1982

[51] Int. Cl.³ ............................................. C07C 121/50
[52] U.S. Cl. ............................ 260/465 R; 260/465 D; 260/465 G; 260/465 H
[58] Field of Search .......... 260/465 R, 465 G, 465 D, 260/465 H

[56] References Cited

U.S. PATENT DOCUMENTS 4,211,721 7/1980 Cotter ............................ 260/465 G Primary Examiner—Delbert R. Phillips
Attorney, Agent, or Firm—James F. Tao; William G. Gosz

[57] ABSTRACT

The instant invention relates to a process for the conversion of an aryl halide into an aryl cyanide, which comprises the steps of:
(a) providing a first electrode and a second electrode of opposite polarity from said first electrode in an electrolyte, said electrolyte comprising an aryl halide and a zerovalent Group VIII metal catalyst complex dissolved in a conductive solvent, wherein said Group VIII metal catalyst complex is capable of catalyzing the conversion of said aryl halide to an aryl cyanide in the presence of cyanide ions and susceptible to reaction with cyanide ions to yield a catalytically inactive Group VIII metal species,
(b) providing cyanide ions in said electrolyte to convert said aryl halide to said aryl cyanide,
(c) providing a flow of current between said electrodes, and
(d) selectively controlling the electrical potential between said first and second electrode to convert said catalytically inactive Group VIII metal species to said zero valent Group VIII metal catalyst complex.

More broadly, the instant invention relates to an improvement in a process for the conversion of a reactant into a reaction product in the presence of a soluble Group VIII metal catalyst complex, wherein said conversion is characterized by the reactant and Group VIII metal catalyst complex combining to form an intermediate, which intermediate may decompose in the presence of a coreactant to said reaction product and said Group VIII metal catalyst complex or said Group VIII metal catalyst may combine with said coreactant to yield a catalytically inactive Group VIII metal species, wherein the improvement comprises electrochemically converting said catalytically inactive Group VIII metal species into said Group VIII metal catalyst complex.

13 Claims, No Drawings

4,499,025

ELECTROCHEMICAL MAINTENANCE OF CATALYST ACTIVITY

FIELD OF THE INVENTION

The instant invention relates to a process for the electrochemical maintenance of catalyst activity. In particular, it has been found that the conversion of aryl halides to products such as aryl cyanides which may be catalyzed by a zerovalent Group VIII metal catalyst, is improved by passing an electric current through the reaction mixture during said conversion to maintain the activity of such zerovalent Group VIII metal catalyst. For example, in the process of the instant invention, aryl chlorides may be converted to their corresponding aryl cyanides by means of a soluble nickel or palladium catalyst complex comprising either nickel or palladium in combination with triphenylphosphine ligands.

BACKGROUND OF THE PRIOR ART

It is well known that various hydrocarbon aryl halides (Ar-X) may be converted to hydrocarbons such as Ar-H and Ar-Ar in the presence of zerovalent nickel catalysts, comprising nickel solubilized by coordinated ligands, e.g. triphenylphosphine ligands. The aryl halide and the nickel triphenylphosphine react to form an oxidative addition product which may be decomposed by heat to yield said hydrocarbons. The oxidative addition products have also been electrochemically decomposed to said hydrocarbons. For example see, Schiavon et al, *J. Chem. Soc. Dalton,* 1074 (1981); Siebelle et al, *J. Chem. Research (M),* 2201 (1980); Bontempelli et al, *Inorg. Chim. Acta,* 42, 211 (1980); Troupel et al, *J. Chem. Res. (S),* 26 (1980); Sibelle et al, *J. Chem. Res. (S),* 268 (1980); and Troupel et al, *J. Organomet Chem.,* 202, 435 (1980).

Hughes, *J. Org. Chem.,* 36, 4073 (1971) and Troupel et al, *J. Chem. Res. (M),* 173 (1980) teach methods for preparing soluble nickel complexes. In both references it is suggested that said soluble nickel complexes form an oxidative addition product with aryl halides, but said product is not decomposed to further products by either author.

Cassar et al, *Advances in Chemistry Series,* 132, 252 (1974) and Cassar et al, *J. Organomet Chem.,* 173, 335 (1979) report that cyanide ion not only promotes deactivation of nickel catalyst complexes but also inhibits the reduction of nickel II complexes similar to those investigated in the above Bontempelli references to the catalytically active nickel complexes.

The authors of the above Bontempelli papers have noted in Bontempelli et al, *J. Chem. Soc. Dalton Trans.,* 1887 (1977); Bontempelli et al, *Anal. Chem.* 49, 1005 (1977); and Seeber et al, *J. Electroanal. Chem.,* 92, 215 (1978) that various nickel II complexes having phosphino and cyano ligands may be electrochemically reduced to active soluble nickel catalyst complexes only at very low temperatures. For example, nickel II phenylphosphine cyanide complexes when electrochemically reduced at temperatures above 0° C. appear to form nickel metal and free phosphine rather than a soluble Ni° complex.

Various patentees teach processes for regenerating catalysts which have become deactivated in use. For example, in U.S. Pat. No. 1,185,500 mercury catalysts are regenerated in a two-step process which reduces various mercury salts to metallic mercury which is subsequently reoxidized to yield catalytically active mercuric salts. Also, U.S. Pat. No. 3,067,276 teaches a three step process for regenerating electrode catalysts. In the third step, regeneration is effected by indirect reduction of the various metal salts comprising said electrode catalysts by using electrolytically produced hydrogen. The electrode catalysts disclosed in this reference are heterogeneous catalysts rather than homogeneous (soluble) catalysts.

In U.S. Pat. No. 3,477,018 a catalyst is non-continuously regenerated by hydrogenation by intermittent contacting of an inactive catalyst with hydrogen. This regeneration process is non-electrolytic, but relies on an electromagnetic method for assessing the activity of a paramagnetic metallic catalyst. Again, the catalyst is a heterogeneous catalyst.

In U.S. Pat. No. 1,431,301 a mercuric salt catalyst is electrolytically regenerated by continuous passage of an oxidizing current. The teaching of this reference is limited to the regeneration of mercuric catalysts. Moreover, the catalyst-reactant system disclosed therein, is a two-phase system, i.e. a heterogeneous catalyst system.

U.S. Pat. Nos. 4,313,803 and 4,313,806 teach a process for electrochemically maintaining the activity of heterogeneous catalysts. In the U.S. Pat. No. 4,813,803 patent, the ratio of metallic copper and a Cu(I) species is adjusted to provide optimum catalytic activity for the conversion of nitriles to amides. The U.S. No. 4,313,806 teaches that the deactivation of Group VIII noble metal catalysts, e.g. palladium metal catalysts, by loss of the Group VIII noble metal, e.g. palladium metal, may be delayed by making the catalyst cathodic with respect to an anode placed in the reaction mixture.

SUMMARY OF THE INVENTION

It has now been found that the activity of soluble (or homogeneous) Group VIII metal catalyst complexes may be maintained by electrochemically converting catalytically inactive Group VIII metal species generated during the use of said catalyst back to a catalytically active state. Thus the instant invention relates to an improvement in a process for the conversion of a reactant into a reaction product in the presence of a soluble Group VIII metal catalyst complex, wherein said conversion is characterized by the reactant and Group VIII metal catalyst complex combining to form an intermediate, which intermediate may decompose in the presence of a coreactant to said reaction product and said Group VIII metal catalyst complex or said Group VIII metal catalyst may combine with said coreactant to yield a catalytically inactive Group VIII metal species, wherein the improvement comprises electrochemically converting said catalytically inactive Group VIII metal species into said Group VIII metal catalyst complex. The instant invention is also applicable to processes wherein the Group VIII metal catalyst complex may combine other components of the reaction system to yield a catalytically inactive Group VIII metal species. Such other components might include a solvent, for the catalyst, the reactant and/or the coreactant; an impurity; a salt utilized to provide conductivity to such solvent, etc.

The process of the instant invention may be illustrated by the electrochemical maintenance of the catalytic activity of a soluble Group VIII metal catalyst complex utilized in the conversion of aryl halides to aryl cyanides. For example, in a process for the conversion of an aryl halide into an aryl cyanide which comprises reacting an aryl halide with a cyanide ion in the presence of a zerovalent Group VIII metal catalyst, wherein said zerovalent Group VIII metal catalyst is susceptible to reaction with said cyanide ion to yield a catalytically-inactive Group VIII metal species, the instant invention comprises an improvement wherein said catalytically inactive Group VIII metal species is electrochemically converted into said zerovalent Group VIII metal catalyst.

More particularly, the instant invention may be illustrated by the conversion of an aryl halide into an aryl cyanide, by a process which comprises the steps of:

(a) providing a first electrode and a second electrode of opposite polarity from said first electrode in an electrolyte, said electrolyte comprising an aryl halide and a zerovalent Group VIII metal catalyst complex dissolved in a conductive solvent, wherein said Group VIII metal catalyst complex is capable of catalyzing the conversion of said aryl halide to an aryl cyanide in the presence of cyanide ions and susceptible to reaction with cyanide ions to yield a catalytically-inactive Group VIII metal species, (b) providing cyanide ions in said electrolyte to convert said aryl halide to said aryl cyanide, (c) providing a flow of current between said electrodes, and (d) selectively controlling the electrical potential or the current between said first and second electrode to convert said catalytically inactive Group VIII metal species to said zero valent Group VIII metal catalyst complex.

The zero valent Group VIII metal catalyst complexes which are useful in the process of the instant invention may be represented by compounds having the general formula $$ML_m$$

wherein M is a zero valent Group VIII metal, e.g. Ni, Co, Fe, Pd, Pt, Ir, Ru, Rh, or Os, preferably Ni or Pd; L is a ligand capable of coordinating with M to form a soluble complex, e.g. CO, $R_3Y$ (wherein R is selected from the group consisting of hydrogen and hydrocarbyl radicals and Y is selected from the group consisting of N, P, As and Sb, preferably P), hydrocarbon residues, e.g. cyclopentadienyl, ethers, and ketones, e.g. acetylacetonate; and m is an integer of from about 2 to about 6, preferably m is 4.

Preferably L represents a phosphino ligand having the general formula $R_3P$ and R is preferably a hydrocarbyl radical comprising an aryl radical, e.g. a $C_6$–$C_{10}$ aryl radical. Thus L may be selected from the group consisting of phenyl, benzyl, para-methylphenyl; naphthyl; meta-tertiarybutylbenzyl; 3,5, dimethylbenzyl; etc.

It is noted that L will be selected to solubilize the zero valent Group VIII metal in the conductive solvent of choice. Therefore excess L may be provided in said electrolyte. For example the molar ratio of L to the zerovalent Group VIII metal may vary from 1:1 to 10:1 or greater. In general, lower molar ratios of L to the zerovalent Group VIII metal are operable if L is a multi-dentate ligand, e.g. a bi-dentate ligand such as 'Diphos' (bis(1,2-diphenyl-phosphino)ethane).

Of course, one skilled in the art will recognize that L may represent more than one ligand, as for example, wherein the zerovalent Group VIII metal catalyst comprises a mixture of ligands, such as one or more aryl phosphine ligands in combination with CO or cyclopentadienyl.

Most preferably R is phenyl and the zero valent Group VIII metal catalyst complex is selected from the group consisting of

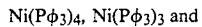

wherein $\phi$ represents the phenyl radical.

The aryl halide may be selected from the group consisting of compounds represented by the general formula:

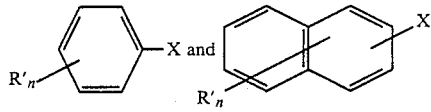

wherein X is a halogen radical selected from the group consisting of Cl, Br and I; R' is a radical selected from the group consisting of halogen radicals, hydrocarbyl radicals, e.g. $C_1$ to $C_6$, preferably methyl radicals, and hydrocarbyl radicals wherein one or more of the hydrogen radicals present therein may be substituted with halogen radicals; and n is an integer of from 0 to 5, preferably from 0 to 1.

As will be further described below, it is preferred that the α-carbon atom of the R' radical be free from hydroxyl, chloro, or nitrogen-containing substituents, e.g. —$NH_2$. In fact the —$NH_2$ group appears to thwart the cyanation of aryl halides by the process of the instant invention when it is directly bound to the same aryl ring as the halogen radical to be cyanated. Aryl halides comprising such substituents at the α-carbon atom of the R' radical form the oxidative addition product with the zero valent Group VIII metal catalyst complex, but decompose to products other than the desired aryl cyanide.

Preferably X is a chlorine radical and R' is a radical selected from the group consisting of

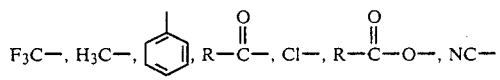

and F-radicals; wherein R is defined above.

The conductive solvents are generally nonaqueous in order to be compatible with the zero valent Group VIII metal catalyst complex. Such solvents include organic solvents such as ethanol, tetrahydrofuran, dimethylformamide, dimethylsulfoxide n-methyl pyrrolidone, hexamethylphosphoramide, dioxane, acetonitrile, dimethyoxyethane, acetone, glycol, and other mono- and di-hydroxy alcohols and mixtures of propylenecarbonate with dimethoxyethane. It is preferred that the solvent be anhydrous or nonaqueous because the presence of water could interfere with the catalytic properties of the zerovalent Group VIII metal catalyst complex. The solvent may comprise two or more mutually soluble liquids, which may themselves be dissolved in a cosolvent.

A salt is dissolved in the solvent to impart conductivity and facilitate the transmission of an electric field therethrough. Salts which dissolve in the electrolyte and have been found useful for imparting to (or increasing the conductivity of) the solvent are lithium perchlorate, LiBF₄ and salts of tetraalkylammonium ions e.g. tetraethylammonium chloride, tetraethylammonium perchlorate, tetraethylammonium fluoroborate, tetrabutylammonium perchlorate, tetrabutylammonium chloride, etc. The major constraint on the selection of a suitable salt is that it should dissolve in the electrolyte and yield a conductive solution without interfering with the cyanation reaction; or the electrochemical maintenance of the activity of the zero valent Group VIII metal catalyst complex.

The cyanide ions are provided from a cyanide ion source which is at least partially soluble in the conductive solvent. The cyanide ion source may be either a salt, e.g. an alkalimetal metal cyanide such as lithium, sodium, or potassium cyanide, a tetraalkylammonium cyanide such tetramethylammonium cyanide or tetraethylammonium cyanide, etc.; an organocyanide e.g. acetone cyanohydrin; or a gas e.g. HCN. The cyanide ions may be added to the conductive solvent as a solution, wherein the solvent for the cyanide ions may be selected from the group consisting of the aforementioned conductive solvents or any other solvent which does not interfere with the cyanation reaction or the electrochemical maintenance of the zerovalent Group VIII metal catalyst complex.

The process of the instant invention may be carried out by providing a first electrode and a second electrode of opposite polarity from said first electrode in an electrolyte comprising one or more of the above aryl halides and one or more of the above zerovalent Group VIII metal catalyst complexes dissolved in a conductive solvent. The electrodes may be carbon either alone or mixed with other substances. Semiconductors and/or metals, e.g. Pt, Ag, Au, etc. may be utilized alone or incorporated with carbon as the electrode. The electrode may be a carbon rod. A Teflon TM/carbon mixture or a carbon/paste mixture may be physically compressed into a suitable electrode.

Neither the chemical composition nor the form of the electrodes is critical to the instant invention provided that the electrode does not reduce the solvent prior to the reduction of the zerovalent Group VIII metal catalyst complex. For example, Pt cannot be used if the conductive solvent comprise ethanol. Thus the prior art rigid electrodes, as well as fluidized electrode particles may be used. As noted below the electrode may be utilized in the form of a loop of carbon fibers. A carbon felt or cloth may also be used as the electrode.

The electrolyte may comprise from 10 to about 80, preferably from 40 to about 60, % by weight of the arylhalide. The zero valent Group VIII metal catalyst complex may vary from 0.01 to about 10, preferably from about 0.2 to about 2, % by weight of said electrolyte.

The electrolyte must also comprise a sufficient amount of the above salts to impart to (or increase the conductivity of) the electrolyte. For example, from about 1% to about 10%, preferably from about 2% to about 5% by weight, of said salt should be included in said electrolyte.

The aryl halide and the zero valent Group VIII metal catalyst complex combine during the course of the process of the instant invention to form an oxidative addition product which is subsequently decomposed in the presence of cyanide ion to yield the corresponding aryl cyanide. The aryl halide can be combined with the zerovalent Group VIII metal catalyst complex to provide said oxidative addition product in the absence of any current or the zerovalent Group VIII metal catalyst complex may be generated in-situ by passing a current through a suitable precursor in the presence of the aryl halide to yield said oxidative addition product.

In either case, the cyanide ions are combined with the electrolyte comprising said oxidative addition product while passing a current through said electrolyte. The potential of said electrodes or the current is adjusted to reduce catalytically inactive species, generated by the combination of said zerovalent Group VIII metal catalyst complex with cyanide ion, to a catalytically active, zerovalent Group VIII metal catalyst complex without electrochemically causing undesirable side reactions. For example, the potential at said electrodes will be maintained at a level insufficient to reduce said conductive solvent to interfering species, or the oxidative addition product to nondesirable side-products.

The arylhalides form the corresponding arylcyanides when cyanated by the process of the instant invention. For example,
para-cyanobenzotrifluoride,
para-cyanotoluene
para-cyano chlorobenzene
meta-cyano chlorobenzene
para-dicyanobenzene
para-cyano fluorobenzene
para-cyano benzophenone, etc. may be formed from the corresponding arylhalides, by means of the instant process.

The process of the instant invention may be conveniently carried out at temperatures of from about 0° to about 200° C., preferably from about 50° to about 150° C. It is noted that the very low temperatures thought necessary by the prior art workers to generate an active nickel catalyst from a nickel II phosphinocyano complex may be avoided without detriment.

The cyanide ions may be added to said electrolyte, comprising said oxidative addition product, over a period of time until the conversion of the aryl halide to the corresponding aryl cyanide is substantially complete. It has been found that the zerovalent Group VIII metal catalyst complex is still catalytically active upon complete conversion of said aryl halide unlike the prior art process wherein the cyanation of arylhalides in the presence of soluble nickel catalyst complexes is carried out in the absence of electrochemical maintenance of catalyst activity or requires excess reducing agent. It is also important to note that much lesser number of coulombs is required to maintain the catalyst activity than would be required for the direct electrochemical reduction of the above oxidative addition product to the arylcyanide. This demonstrates that the current is utilized to maintain the activity of the catalyst, rather than reducing the oxidative addition product to the desired aryl cyanide.

The following examples are preferred embodiments of the instant invention.

EXAMPLE 1

Cyanation of Aryl Halides With a Zerovalent Nickel Catalyst Complex

The electrochemical cell used was a typical 3-compartment cell modified for operation under an inert atmosphere. The working and auxillary electrodes consisted of several 1–2" diameter loops of carbon fiber secured by a collar of heat-shrinkable Teflon ™ tubing. Electrical contact was made using alligator chips soldered to a length of copper wire which was sealed in ¼″ glass tubing with a quick-setting epoxy. HMS carbon fibers available from Hercules Co. are suitable for the working and auxillary electrodes but any electrode material which has not been coated with a substance which inhibits electron transfer and at which the zerovalent Ni catalyst complex (NiL$_n$) is formed at potentials less negative than that at which the reduction of the ethanol (or other conductive solvent) occurs would also be suitable. The reference electrode used was of the double junction type. The actual reference electrode consisted of a polished silver wire immersed in an ethanolic solution of 0.1M AgBF$_4$ (silver tetrafluoroborate) contained within a glass tube fitted at one end with a glass frit or other device to insure slow electrolyte leakage. The reference electrode assembly was inserted into a second "leaky" glass tube containing 0.1M tetrabutylammonium perchlorate in ethanol. Typically, the working electrode compartment of the cell was loaded with 0.25 to 1.0 mmoles NiL$_n$, 0.75 to 3.0 mmoles L (e.g., triphenylphosphine), 100–150 mmoles of the aryl halide and 10 mmoles naphthalene (as an internal gas chromatograph standard) in an inert atmosphere glove box. The cell was then removed from the glove box and a volume of degassed 0.1M tetraethylammonium chloride in ethanol was injected into each of the three cell compartments to bring the solution level up to contact the electrodes. (For example, in the cell used in this experiment, 40 ml of 0.1M tetraethylammonium chloride in ethanol was added to the working electrode compartment.) The cell and its contents were then heated to 55° C. and typically maintained at this temperature for 30–90 minutes until oxidative addition of the aryl halide was complete as judged by the change in the color of solution in the working electrode compartment. The controlled addition of an ethanolic solution of tetraethylammonium cyanide was then begun simultaneous with the imposition of a working electrode potential of $-1.2$ to $-1.5$ V. vs. Ag/Ag$^+$. Typically, a 3–4M ethanolic solution of tetraethylammonium cyanide was used and added at the rate of 1–2 ml/hr. However, other cyanating agents could be used without deviating from the scope of this invention, e.g. acetone cyanohydrin.

The results obtained for several aryl halides are listed in Table 1. Note that no attempt was made to optimize the number of catalyst turnovers reported in Table 1. The number of catalyst turnovers is a measure of how many molecules of product per molecule of catalyst is obtained, prior to deactivation or completion of the reaction. Note the substantial improvement in the instant process. Moreover it is important to note that the number of electrons consumed per mole of product formed is very low. This demonstrates that catalyst activity is maintained by intercepting various catalytically inactive Group VIII metal species produced in side reactions rather than the product being formed by direct reduction of the oxidative addition product.

The experiments were run under either controlled potential conditions or at a constant applied current of 5 mA. For example, p-chlorobenzotrifluoride was run under controlled potential conditions but, the remaining experiments were conducted at a constant applied current of 5 mA. Constant current operation is more commercially practical.

Examples of aryl halides which were not cyanated under the usual homogeneous conditions in the presence of the particular NiL$_n$ selected herein include ortho-chlorobenzotrifluoride, para-chlorobenzamide, para-chlorobenzyl alcohol and parachlorobenzyl amine. All of these aryl chlorides oxidatively added to the NiL$_n$ but the corresponding nitrile was not detected in the reaction mixture. It was found that the corresponding ortho bromide (ortho-bromobenzotrifluoride) would form the cyanide. However, it appears that benzyl substituents (—CH$_2$X' wherein X' is selected from the group consisting of —Cl, —OH and —NH$_2$) and phenyl amides $$\begin{array}{c}(-\overset{}{\underset{\parallel}{\text{C}}}\text{NH}_2)\\ \text{O}\end{array}$$

interfere with the nickel catalyzed cyanation reaction.

When nitro groups (—NO$_2$) and aldehyde groups (—CHO) were substituted on the arylhalide, (e.g. as in para-chlorobenzaldehyde and 2-nitro-5-chlorobenzotrifluoride), a complicated mixture of products was obtained from the addition product.

It is believed that the above aryl halides could be successfully cyanated by means of higher temperature reactions or other forcing conditions.

TABLE 1

Comparison of Instant Process and Homogeneous Catalysis for the Cyanation of Aryl Chlorides.

| ArX | Product | Catalyst Turnover Homogeneous | Catalyst Turnover Instant Process | Electrons Consumed Per Mole of Product Made |
|---|---|---|---|---|
| F$_3$C—⌬—Cl | F$_3$C—⌬—CN | 32 | 142 | 0.04 |
| F$_3$C—⌬ (Cl ortho) | F$_3$C—⌬ (CN ortho) | 55 | 124 | 0.03 |
| H$_3$C—⌬—Cl | H$_3$C—⌬—CN | 25 | 160 | 0.03 |

TABLE 1-continued
Comparison of Instant Process and Homogeneous Catalysis for the Cyanation of Aryl Chlorides.

| ArX | Product | Catalyst Turnover Homogeneous | Catalyst Turnover Instant Process | Electrons Consumed Per Mole of Product Made |
|---|---|---|---|---|
| H₃C—⌬—Cl | H₃C—⌬—CN | 54 | 230[a] | 0.02 |
| ⌬—C(=O)—⌬—Cl | ⌬—C(=O)—⌬—CN | 84 | 200[a] | 0.04 |
| F—⌬—Cl (ortho Cl) | F—⌬—CN (ortho CN) | 46 | 185 | 0.04 |
| Cl-naphthyl | CN-naphthyl | 16 | 200[a] | 0.04 |
| Cl—⌬—Cl | NC—⌬—CN | 46 | 81[b] | 0.03 |

[a]Reaction was arbitrarily terminated, catalyst was still active.
[b]Insoluble product coated electrode and probably prevented further turnovers.

EXAMPLE 2
Zerovalent Palladium Catalyzed Cyanation of Aryl Halides

The reactions below were run in a manner similar to Example 1 except a more severe temperature (130° C. instead of 55° C.) was used, and the conductive solvent was dimethylformamide. The catalyst was Pd(L)₄, wherein L is triphenylphosphine.

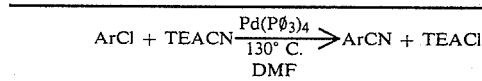

| ArCl | TEACN Addition Rate, mm/hr | Catalyst Homog. | Turnovers Instant Process | Electrons Consumed/ Mole Product |
|---|---|---|---|---|
| F₃C—⌬—Cl | 1.4 | 58 | 113 | 0.24 |
| F₃C—⌬—Cl | 2.1 | 38 | 166 | 0.11 |
| F₃C—⌬—Cl | 3.5 | 8 | 162 | 0.06 |
| H₃C—⌬—Cl | 2.1 | 0 | ~2 | 0.10 |
| F₃C—⌬ (ortho Cl) | 1.4 | 18 | 130 | 0.14 |
| F₃C—⌬ (ortho Cl) | 1.0 | Trace | Trace | — |

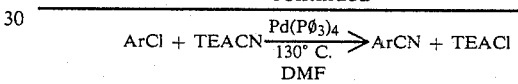

| ArCl | TEACN Addition Rate, mm/hr | Catalyst Homog. | Turnovers Instant Process | Electrons Consumed/ Mole Product |
|---|---|---|---|---|
| ⌬—Cl | 1.0 | 0 | 96 | 0.25 |

ArCl = Aryl chloride
TEACN = Tetraethylammonium cyanide
DMF = Dimethylformamide
TEACl = Tetraethylammonium chloride In the first 3 runs, above, it is demonstrated that the process of the instant invention can tolerate rapid addition of CN⁻. The control reactions deactivate more quickly as the rate of CN⁻ addition increases.

A reaction with para-chlorotoluene was not obtained using the palladium catalyst complex. This compound was very reactive in the nickel catalyst complex system, however.

The reaction of meta-chlorotoluene with the palladium catalyst complex is more efficient than with the nickel catalyst complex system.

Trace amounts of ortho-cyanobenzotrifluoride were formed from ortho-chlorobenzotrifluoride. While no improvement was observed, the results indicate that unreactive ortho compounds may react if the palladium catalyst complex is made more active. (Ortho substituted aryl chlorides tend to be unreactive with the nickel catalyst complex system).

The cyanation of chlorobenzene in the presence of the zerovalent-palladium catalyst complex is significant since this substrate was rather unreactive in the analogous nickel system.

Again, the number of electrons consumed per mole of product was very low, demonstrating that the current passed through the reaction mixture is utilized to maintain the activity of the catalyst and does not reduce the oxidative addition product of the zerovalent palladium and the aryl halide directly.

What is claimed is:

1. In a process for the conversion of an aryl halide into an aryl cyanide which comprises reacting an aryl halide with a cyanide ion in the presence of a zero valent Group VIII metal catalyst, said aryl halide being selected from the group consisting of compounds having the general formula:

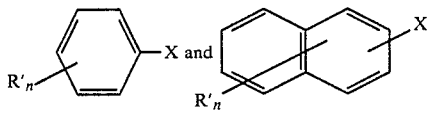

wherein X is a halogen radical selected from the group consisting of —Cl, —Br and —I; R' is a radical selected from the group consisting of halogen radicals, hydrocarbyl radicals and hydrocarbyl radicals wherein one or more of the hydrogen radicals present therein may be substituted with halogen radicals; and n is an integer of from 0 to 1, and wherein said zero valent Group VIII metal catalyst is susceptible to reaction with said cyanide ion to yield a catalytically-inactive Group VIII metal compound, said zero valent Group VIII metal catalyst being represented by compounds having the general formula:

MLm wherein M is a Group VIII metal, L is a ligand capable of coordinating with M selected from the group consisting of CO; ligands represented by the general formula $R_3Y$ wherein R is independently selected from the group consisting of hydrogen and hydrocarbyl radicals and Y is selected from the group consisting of N, P, As and Sb; hydrocarbon residues; ethers; and ketones, m being an integer of from about 2 to about 6, the improvement comprising electrochemically converting said catalytically-inactive Group VIII metal compound into said zero valent Group VIII metal catalyst.

2. The process of claim 1 wherein X is a chlorine radical.

3. The process of claim 2 wherein R' is a radical selected from the group consisting of

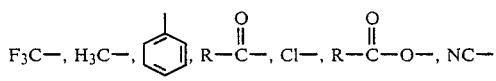

and F-radicals, and wherein R is selected from the group consisting of $C_6$ to $C_{10}$ aryl radicals.

4. The process of claim 3 wherein Y is P and R is a phenyl radical.

5. The process of claim 1 wherein said cyanide ion is provided by a tetraalkylammonium cyanide.

6. The process of claim 5 wherein said cyanide ion is provided by adding an ethanolic solution of tetraalkylammonium cyanide to an ethanolic solution of said aryl halide and said zerovalent nickel catalyst.

7. A process for the conversion of an aryl halide into an aryl cyanide, which comprises the steps of:

(a) providing a first electrode and a second electrode of opposite polarity from said first electrode in an electrolyte, said electrolyte comprising an aryl halide and a zero valent Group VIII metal catalyst complex dissolved in a conductive solvent, wherein said Group VIII metal catalyst complex is capable of catalyzing the conversion of said aryl halide to an aryl cyanide in the presence of cyanide ions and susceptible to reaction with cyanide ions to yield a catalytically inactive Group VIII metal species, said zero valent Group VIII metal catalyst being represented by compounds having the general formula:

MLm wherein M is a Group VIII metal, L is a ligand capable of coordinating with M selected from the group consisting of CO; ligands represented by the general formula $R_3Y$ wherein R is independently selected from the group consisting of hydrogen and hydrocarbyl radicals and Y is selected from the group consisting of N, P, As and Sb; hydrocarbon residues; ethers and detones, m being an integer from about 2 to about 6; said aryl halide being selected from the group consisting of compounds represented by the general formula:

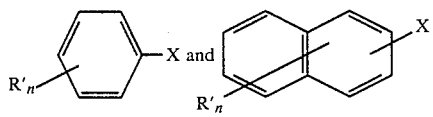

wherein X is a halogen radical selected from the group consisting of —Cl, —Br and —I; R' is a radical selected from the group consisting of halogen radicals, hydrocarbyl radicals and hydrocarbyl radicals wherein one or more of the hydrogen radicals present therein may be substituted with halogen radicals; and n is an integer of from 0 to 1, (b) providing cyanide ions in said electrolyte to convert said aryl halide to said aryl cyanide, (c) providing a flow of current between said electrodes, and (d) selectively controlling the electrical potential or the current between said first and second electrode to convert said catalytically inactive Group VIII metal species to said zero valent Group VIII metal catalyst complex.

8. The process of claim 7 wherein X is a chlorine radical.

9. The process of claim 8 wherein R' is a radical selected from the group consisting of

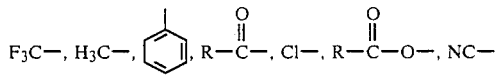

and F-radicals and wherein R is selected from the group consisting of $C_6$ to $C_{10}$ aryl radicals.

10. The process of claim 9 wherein Y is P and R is a phenyl radical.

11. The process of claim 7 wherein said conductive solvent is selected from the group consisting of ethanol and dimethylformamide.

12. The process of claim 10 wherein M is Ni and said conductive solvent is ethanol.

13. The process of claim 10 wherein M is Pd and said conductive solvent is dimethylformamide.

* * * * *